US007785326B2

(12) United States Patent
Green et al.

(10) Patent No.: US 7,785,326 B2
(45) Date of Patent: Aug. 31, 2010

(54) SYSTEM FOR INTRAMEDULLARY ROD FIXATION AND METHOD THEREFOR

(76) Inventors: Daniel W. Green, 5075 Fieldston Rd., Bronx, NY (US) 10471; Joseph L. Molino, 2 Aura Dr., Valley Cottage, NY (US) 10989

( * ) Notice: Subject to any disclaimer, the term of this patent is extended or adjusted under 35 U.S.C. 154(b) by 1254 days.

(21) Appl. No.: 11/250,498

(22) Filed: Oct. 14, 2005

(65) Prior Publication Data
US 2007/0100342 A1    May 3, 2007

(51) Int. Cl.
*A61B 17/56* (2006.01)
(52) U.S. Cl. .......................... 606/64; 606/62; 606/304
(58) Field of Classification Search ............ 606/62–68, 606/300, 304, 309, 314, 318, 87, 96, 98, 606/104; 411/383, 393, 395, 315
See application file for complete search history.

(56) References Cited

U.S. PATENT DOCUMENTS

| | | | | |
|---|---|---|---|---|
| 2,168,000 A * | 8/1939 | Schaurte | ...................... | 411/392 |
| 2,658,508 A * | 11/1953 | Gibson | ......................... | 606/70 |
| 4,281,649 A * | 8/1981 | Derweduwen | ................. | 606/64 |
| 4,622,959 A * | 11/1986 | Marcus | ......................... | 606/64 |
| 4,827,917 A * | 5/1989 | Brumfield | ..................... | 606/64 |
| 4,875,475 A * | 10/1989 | Comte et al. | .................. | 606/64 |
| 4,976,258 A | 12/1990 | Richter et al. | | |
| 5,118,236 A * | 6/1992 | Rodriguez et al. | .......... | 411/378 |
| 5,489,284 A * | 2/1996 | James et al. | ................... | 606/62 |
| 6,221,074 B1 * | 4/2001 | Cole et al. | .................... | 606/62 |
| 6,235,031 B1 * | 5/2001 | Hodgeman et al. | ............ | 606/64 |
| 6,270,499 B1 | 8/2001 | Leu et al. | | |
| 6,379,360 B1 * | 4/2002 | Ackeret et al. | ................ | 606/67 |
| 6,402,753 B1 | 6/2002 | Cole et al. | | |
| 6,579,293 B1 | 6/2003 | Chandran | | |
| 7,347,861 B2 * | 3/2008 | Johnstone | ..................... | 606/62 |

OTHER PUBLICATIONS

The Titanium Elastic Nail System (Technique Guide), SYNTHES, 1998.
The AO/ASIF Unreamed Tibial Nail, SYNTHES, 1992.

* cited by examiner

*Primary Examiner*—Thomas C Barrett
*Assistant Examiner*—Christine L Nelson
(74) *Attorney, Agent, or Firm*—Lawrence G. Fridman

(57) ABSTRACT

A system and method for securing an intramedullary rod in a medullary canal of a long bone is provided. The system includes an intramedullary rod and a screw assembly for receiving the rod. The screw assembly has a transverse receiving bore for receiving the intramedullary rod and a securing member movable toward the bore for securing the rod to the screw assembly. An alignment jig may also be provided for aligning the rod with the receiving bore during installation.

5 Claims, 8 Drawing Sheets

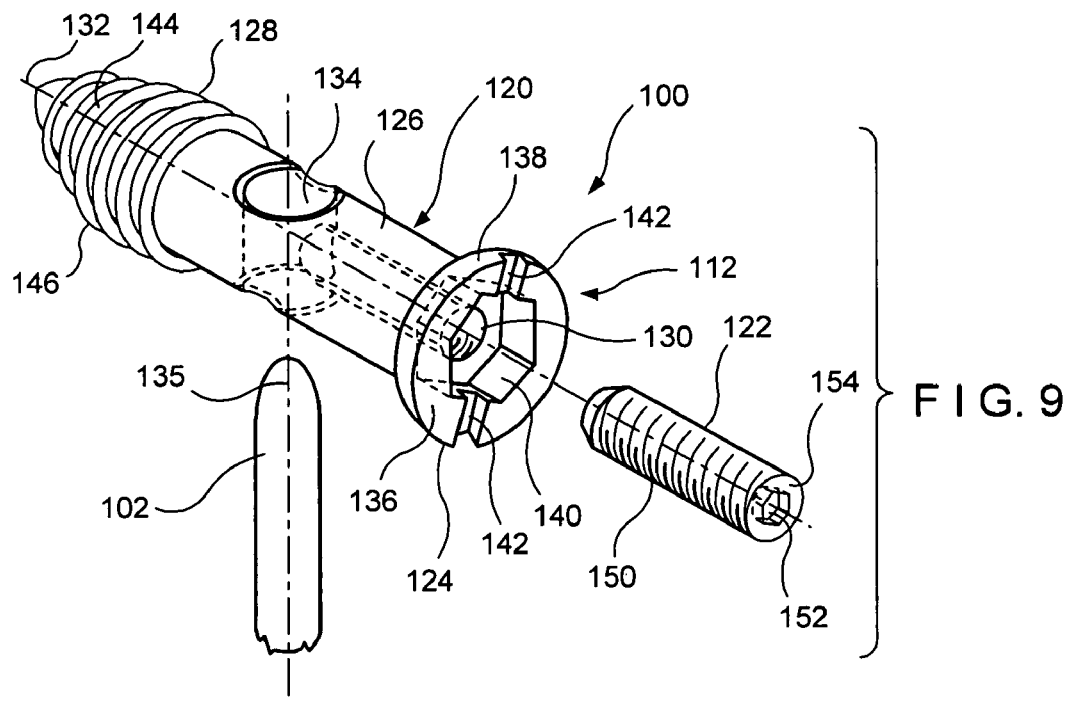
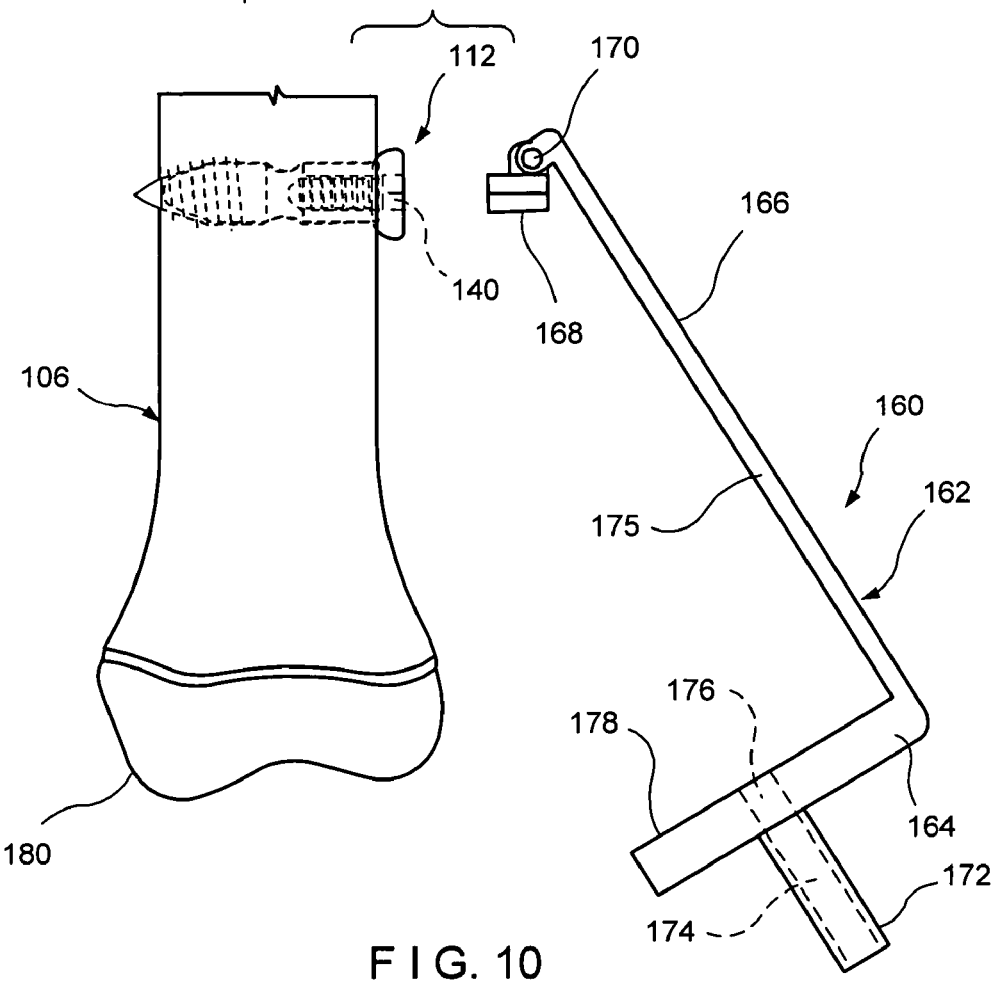
FIG. 9
FIG. 10

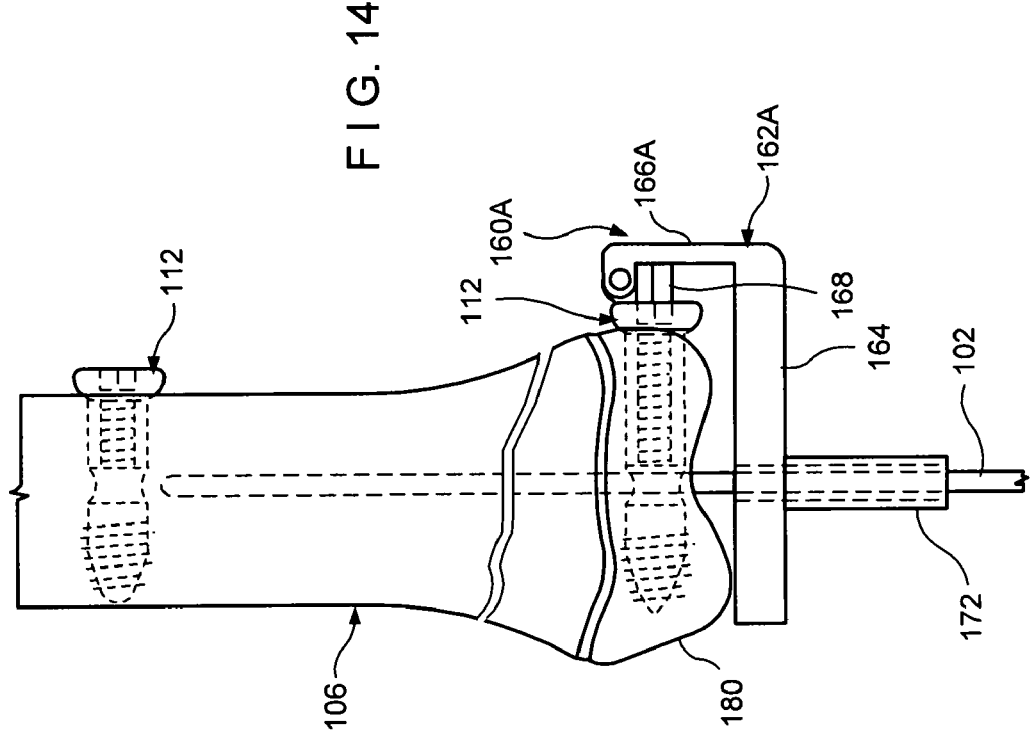
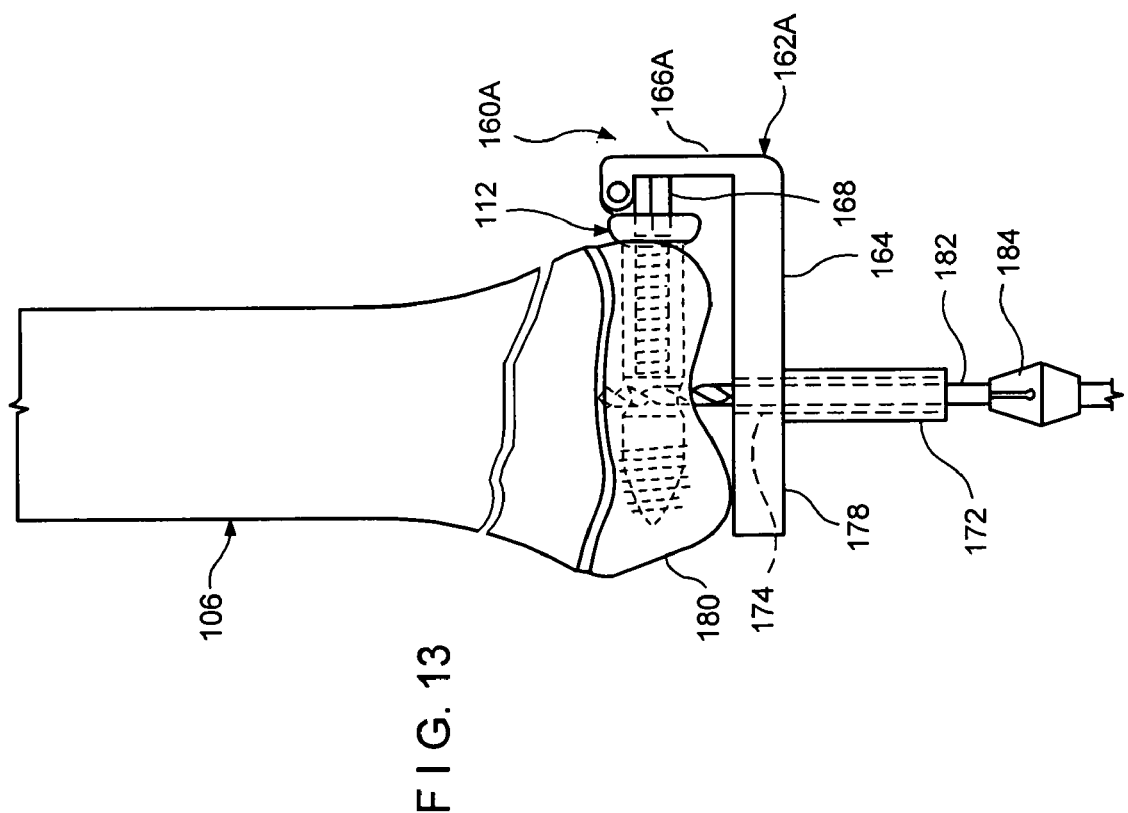

SYSTEM FOR INTRAMEDULLARY ROD FIXATION AND METHOD THEREFOR

BACKGROUND OF THE INVENTION

1. Field of the Invention

The present invention relates generally to the treatment of bone fractures or abnormal bone conditions which require osteotomies, and more particularly to an intramedullary rod system for stabilizing bone segments.

2. Description of Prior Art

The fracture of certain bones, such as the femur, tibia, ulna, radius and humerous, requires substantial immobilization of the fractured bone sections in an abutting relationship during the healing process. Any longitudinal, transverse, or rotational movement of one fractured bone section relative to the other may cause a substantial delay in healing time or improper healing of the bone itself. In general, prior art provides various internal fixation approaches that have been used to immobilize the area surrounding the fracture site.

One approach involves driving metallic pins through the two sections of bone to be joined and connecting them to one or more plates bearing against the external surface of the bones. However, such an arrangement may cause injury to the surrounding outer layer and decrease blood supply and delay or inhibit bone healing. Plates also tend to shield the bone from stress and decrease the strength of the underlying bone.

Another approach for treating fractures involves the use of an intramedullary nail or rod which is inserted into the medullary canal of the bone, so as to be affixed therein. After complete healing of the bone at the fracture site, the rod may be removed through a hole drilled in the proximal or distal end of the bone.

A prior art flexible intramedullary nailing technique for affixing and mobilizing bone segments is illustrated in FIG. 1. This technique includes drilling oblique lateral and medial openings 12, 14 in the fractured bone 10 above the physis 16, then inserting pre-bent flexible stainless steel or titanium nails 18 and 20 (shown in dashed line), which are typically 2-4 mm in diameter, into the bone interior or canal 22 through the openings in a retrograde manner. Prior to insertion, each nail 18, 20 must be bent or curved such that their apexes 24, 26 are at the level of the fracture 25. Since the fracture may be oblique to a central axis of the bone as shown in FIG. 1, the nails 18, 20 may be bent at different locations. Using fluoroscopy to visualize rod progression and placement, the nails are advanced through the bone until they cross the fracture. The nails are then cut to length. Distal ends 28 and 30 of the nails are left extending slightly into the soft tissue surrounding the bone 10.

Although flexible nails have been utilized by some doctors (primarily in pediatric patients with small diameter long bones), there are drawbacks to their use. For instance, the nails are not securely fixed within the intra medullary canal. Moreover, flexible nails lack the rotational stability of rigid nails and normally cannot be used in highly unstable or comminuted fractures.

FIG. 2 depicts another prior art solution that makes use of a flexible rod 32 (shown in dashed line). The rod 32 is inserted into the medullary canal 22 of the tibia 10. The rod 32 is inserted manually as far as possible. An image intensifier is used to locate the distal end 34 of the rod. The proximal end 36 of the rod is then bent over in an attempt to anchor the rod to the bone area. The distal end 34 may be left unanchored to allow for growth of the bone, resulting in unpredictable positioning of the rod. Alternatively, the distal end 34 may also be bent over and fixedly attached to the distal end of the bone, but is nevertheless haphazard and imprecise.

FIGS. 3 and 4 show another prior art solution involving an unreamed tibial nail 40 (shown in dashed line). The nail 40 is inserted into the medullary canal 22 of the tibia 10, medial to the patellar tendon and as superior as possible. The nail 40 includes a plurality of openings 42 for receiving screws 44. Once in position, the location of the openings 42 are determined by fluoroscopy and the screws 44 are inserted transversely through the bone and openings 42 for anchoring the nail 40 in place. Although this type of system may be acceptable for bones having relatively large cross sections, it is difficult to implement in smaller bone structures due to size restraints. This is especially typical pediatric cases. For example, a typical nail may have a diameter in the range of 8-9 mm and the screws may have a thread diameter of approximately 4 mm in order to properly secure the nail to the bone. For pediatric situations or other cases where it may be impractical to insert a large diameter nail into a small bone, a suitable nail may have a diameter in the range of 2-4 mm and thus would require a screw with a substantially smaller thread diameter. However, forming a hole in the 2-4 mm nail would be quite difficult, and the provision of a substantially smaller screw to fit in the hole would not provide sufficient cross-pinning to isolate movement of the nail or to fix it in a desired position.

BRIEF SUMMARY OF THE INVENTION

According to one aspect of the invention, a screw assembly for securing an intramedullary rod in a medullary canal of a bone is provided. The screw assembly includes a screw body with a shaft and at least one receiving bore that extends transversely through the shaft. The bore is adapted to receive an intramedullary rod. A securing member is movable toward the bore to thereby secure the rod to the screw assembly.

According to a further aspect of the invention, a system for securing an intramedullary rod in a medullary canal of a bone is provided. The system includes an intramedullary rod and a screw assembly for receiving the rod. The screw assembly has a receiving bore extending transversely therethrough for receiving the intramedullary rod and a securing member movable toward the receiving bore for securing the rod to the screw assembly. An alignment jig may also be provided for aligning the rod with the receiving bore during installation.

According to yet a further aspect of the invention, a method for installing an intramedullary rod within a medullary canal of a bone is also provided. The method comprises providing a screw with a transverse bore, installing the screw into the bone such that the transverse bore is within the medullary canal, and inserting an intramedullary rod into the medullary canal and through the transverse bore. The intramedullary rod may then be secured to the screw.

BRIEF DESCRIPTION OF THE DRAWINGS

The foregoing summary as well as the following detailed description of the preferred embodiments of the present invention will be best understood when considered in conjunction with the accompanying drawings, wherein like designations denote like elements throughout the drawings, and wherein:

FIG. 9 is an exploded perspective view of the nailing system in accordance with the present invention;

FIG. 10 is a front elevational view of an alignment jig together with an installed bone screw for aligning an intramedullary rod with a transverse opening in the screw in accordance with the present invention;

FIG. 13 is a front elevational view of an alignment jig in accordance with a further embodiment of the invention in proper position for boring a hole through the bone;

FIG. 14 is a view similar to FIG. 13 and illustrating insertion of the intramedullary rod through the bored hole and screws.

It is noted that the drawings are intended to depict only typical embodiments of the invention and therefore should not be considered as limiting the scope thereof. It is further noted that the drawings are not necessarily to scale. The invention will now be described in greater detail with reference to the accompanying drawings.

DETAILED DESCRIPTION OF THE INVENTION

Figures 1, 2:
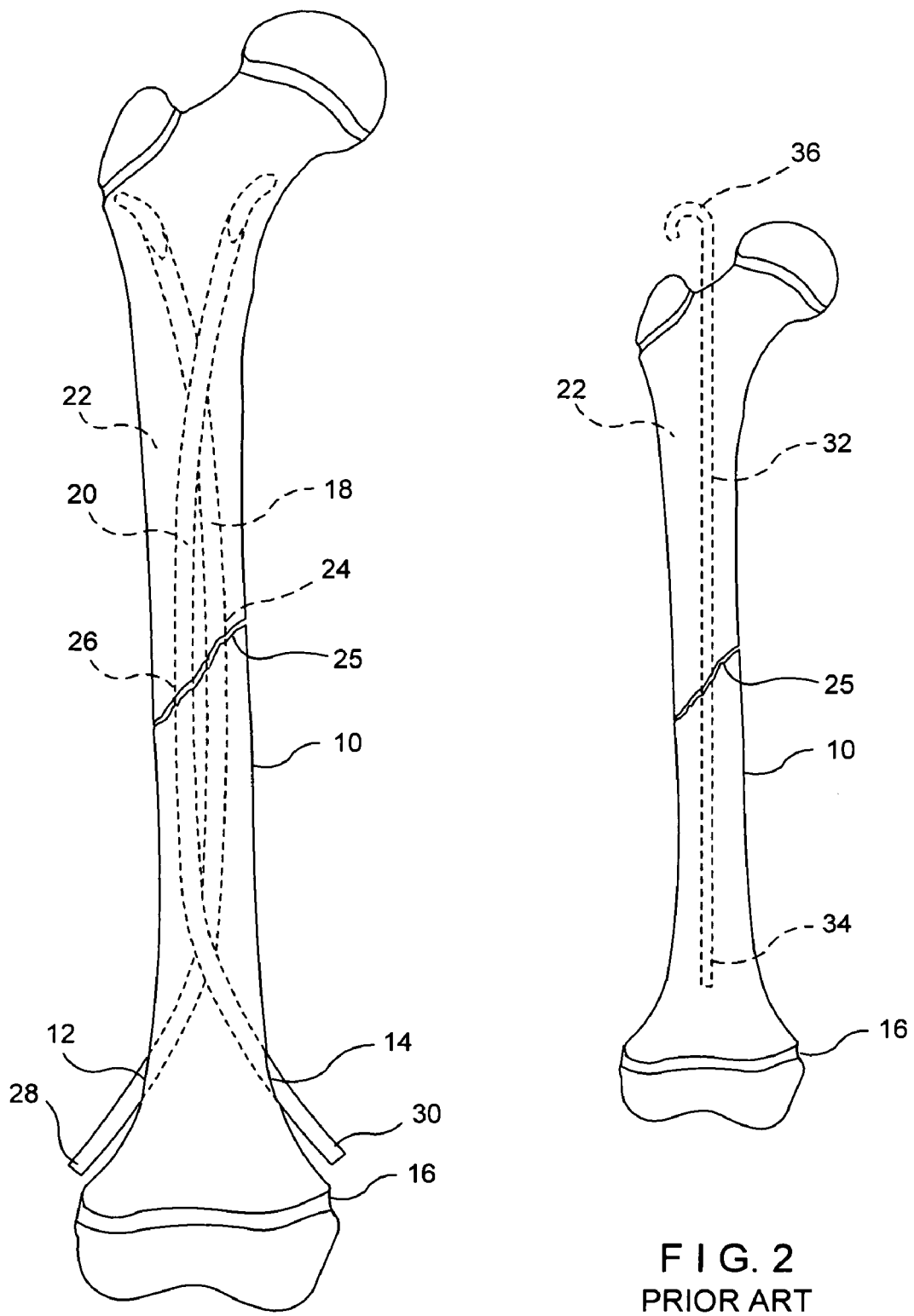
FIG. 1 is a front elevational view of a prior art intramedullary nailing system for affixing and mobilizing separated bone segments of a bone structure.
FIG. 2 is a front elevational view of a further prior art intramedullary nailing system.
Figures 3, 4:
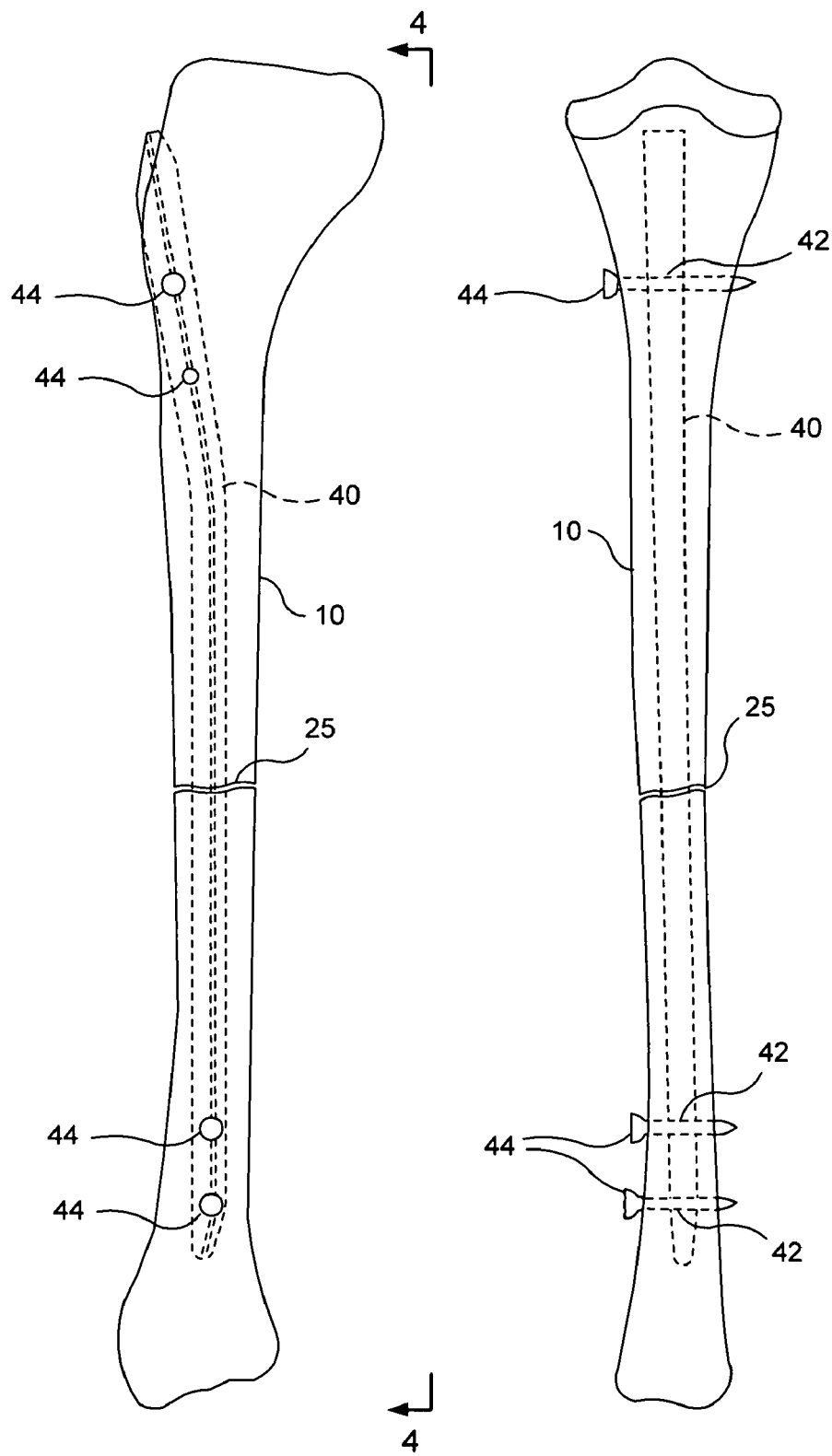
FIG. 3 is a front elevational view if yet a further prior art intramedullary nailing system.
FIG. 4 is a side elevational view as viewed from section plane 4-4 of FIG. 3.
Figure 5:
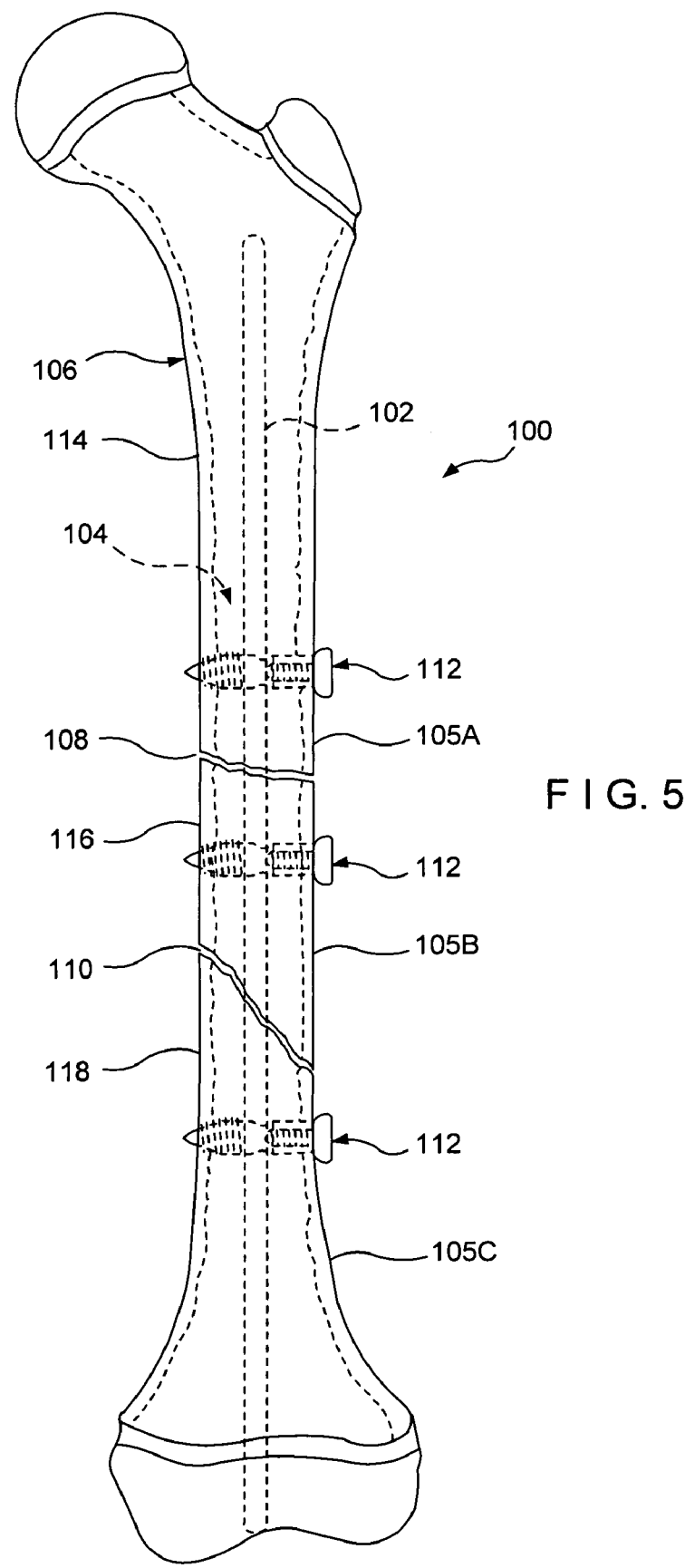
FIG. 5 is a front elevational view of an intramedullary nailing system in accordance with an exemplary embodiment of the present invention for affixing and/or mobilizing separated bone segments of a bone structure.
Figure 6:
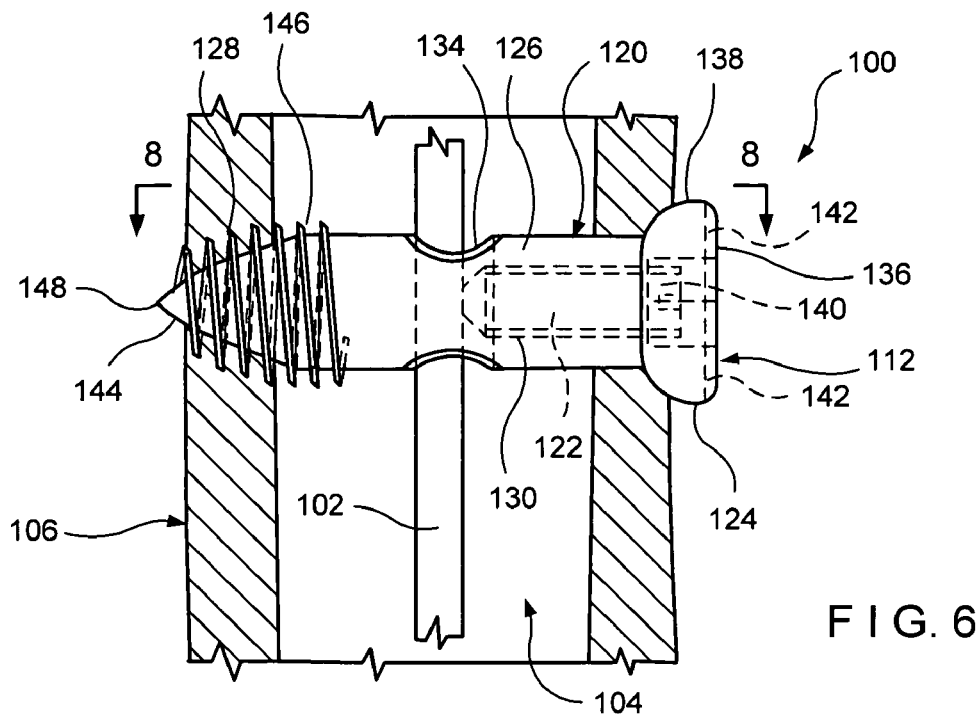
FIG. 6 is an enlarged front view of a portion of the nailing system of FIG. 5 showing a bone segment in cross section.
Figure 7:
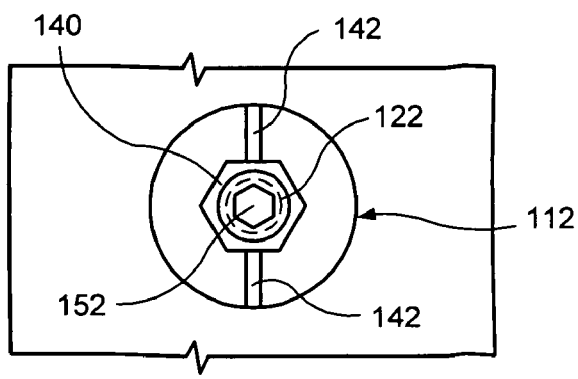
FIG. 7 is a side elevational view of the nailing system of FIG. 6.

Referring to the drawings, and to FIG. 5 in particular, an intramedullary nailing system 100 in accordance with an exemplary embodiment of the present invention for affixing and/or mobilizing two or more separated bone segments, such as segments 114, 116, and 118, of a bone structure 106 is illustrated. The system 100 preferably includes an intramedullary nail or rod 102 (shown in hidden line) that is adapted to extend into the medullary canal 104 (also shown in hidden line) of the bone structure 106 with one or more fractures 108, 110 and a screw assembly 112 that anchors the rod 102 within the medullary canal to secure the bone segments together during the treatment process.

The system 100 of the present invention is especially suitable in pediatric orthopedics for fixation of fractured bones such as the tibia, femur and humerus, complications caused by osteogenesis imperfecta, pseudoarthrosis of the tibia, and so on. However, it will be understood that the present invention is not limited to treatment of the afore-mentioned bones for the afore-mentioned conditions, but is also applicable to a wide variety of bone structures (such as the fibula, ulna and radius), bone sizes and conditions for both pediatric and general orthopedics.

The intramedullary rod 102 is preferably of conventional construction and can be formed of various materials, such as titanium or stainless steel. The rod 102 is also preferably circular in cross section, and of a sufficiently small diameter to fit within the medullary canal of the particular bone structure to be treated. By way of example, rods with diameters of 2, 2.5, 3, and 4 mm are commonly used for pediatric applications. It will be understood that the intramedullary rod 102 is not limited to the particular sizes, cross sectional shape or materials mentioned above, but may be constructed of different sizes, different cross sectional shapes such as square, triangular, oval, and so on, and different materials such as metals, ceramics, plastics, composites, or combinations thereof.

Referring now to FIGS. 6-9, the screw assembly 112 preferably includes a screw body 120 with a locking member 122 positionable within an internal cavity 130 of the screw body for fixing the rod 102 to the screw assembly 112. The screw body 120 has a shaft 126 with a head portion 124 formed at one end thereof and an auger portion 128 formed at an opposite end.

The shaft 126 includes a transversely extending receiving bore 134 and the longitudinally extending internal cavity 130 that substantially coincides with a central axis 132 of the shaft and that intersects the internal cavity. Preferably, a central axis 135 of the receiving bore 134 and the central axis 132 of the shaft 126 (see FIG. 9) are substantially perpendicular to each other. However, it will be understood that the angle between the receiving bore and the internal cavity can vary, depending on the particular orthopedic application. The internal cavity 130 is preferably internally threaded for receiving and engaging the locking member 122. The receiving bore 134 can have a smooth inner surface and is sized to receive the intramedullary rod 102.

The head portion 124 preferably has a generally flat front surface 136 and a curved rear surface 138 that extends between the front surface 136 and the shaft 126. In one embodiment of the invention, the diameter of the head portion 124 is approximately 1.5 times the diameter of the shaft 126. However, it will be understood that the relative dimensions of the head portion and shaft can greatly vary. A hexagonally-shaped depression 140 extends into the head portion 124 from the front surface 136 and intersects with the front end of the internal cavity 130. The depression 140 is adapted to receive a corresponding suitably shaped or hexagonally-shaped tool (not shown) for turning the screw assembly 112 during installation and removal as well as for alignment purposes, as will be described in greater detail below.

Alignment indicator marks 142, preferably in the form of slots, are formed in the front surface 136 of the head portion 124 at opposite sides of the depression 140. The slots 142 are preferably parallel with the central axis 135 of the receiving bore 134 so that the bore can be properly oriented during installation of the screw assembly 112. It will be understood that the slots 142 can be replaced with other marks, ticks, protrusions, or any other visually distinguishable indicating means for specifying the orientation of the receiving bore 134. It will be further understood that the head portion 124, including the depression 140, is not limited to the particular shape as shown and described, but may assume a wide variety of shapes and tool engaging configurations.

The auger portion 128 includes a conical section 144 with a spiral thread 146 that gradually diminishes in thread diameter toward the tip 148 to form a self-tapping configuration that facilitates boring into the bone structure as well as attachment of the screw assembly to the bone structure during installation. It will be understood that the auger portion 128 is not limited to the conical shape, but may alternatively be cylindrical with a uniform screw thread diameter or of any other suitable configuration.

As best illustrated in FIG. 9, the locking member 122 is preferably in the form of a set screw with outer threads 150 that engage the inner threads of the internal cavity 130. A hexagonally-shaped, for example, depression 152 is formed in an end face 154 of the locking member 122. The depression 152 is adapted to receive a corresponding or hexagonally-shaped tool (not shown) for turning the locking member 122 inside the internal cavity 130 toward or away from the receiving bore 134 to thereby clamp or release the intramedullary rod 10 within the receiving bore.

Figure 11:
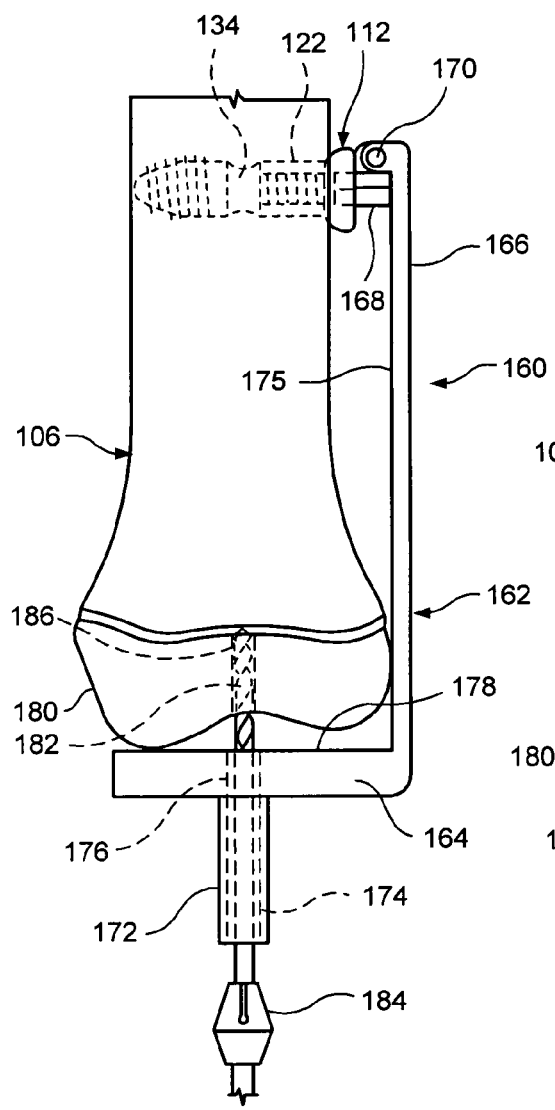
FIG. 11 is a view similar to FIG. 10 with the alignment device in proper position for boring a hole through the bone.
Figure 12:
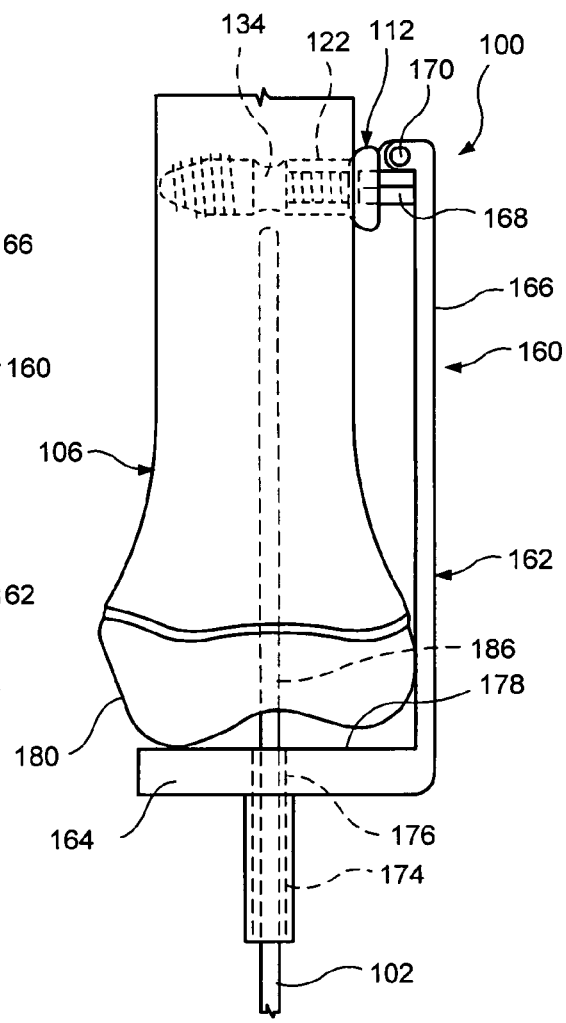
FIG. 12 is a view similar to FIG. 10 and illustrating insertion of the intramedullary rod through the bored hole in alignment with the bore of the screw.

In order to facilitate alignment of the intramedullary rod 102 with the receiving bore 134 of the screw assembly 112 during installation, an alignment jig 160 in accordance with the present invention is provided, as shown in FIGS. 10-12. The alignment jig 160 includes a base member 162 with a first leg 164 and a second leg 166 that extends upwardly from the first leg. Preferably, the first and second legs are substantially perpendicular to each other. A hexagonally-shaped, for example, bar 168 is pivotally connected to an outer free end of the second leg 166 at a pivot joint 170. The bar 168 is sized and shaped to be received within the respective or hexagonal depression 140 of the screw head portion 120. A tubular guide member 172 extends downwardly from the first leg 164 and includes a central bore 174 (shown in hidden line) that substantially coincides with an opening 176 (shown in hidden lines) in the first leg 164. Preferably, a proximal surface 178 of the first leg 164 is planar. The distance between a centerline of the central bore 174 and an inner surface 175 of the second leg 166 (or outer end of the hexagonal bar 168) is preferably chosen so that when the alignment jig 160 is in the position shown in FIG. 11, the central bore 174 will be aligned with the medullary canal of the bone and the receiving bore 134 of the screw assembly 112.

Figure 8:
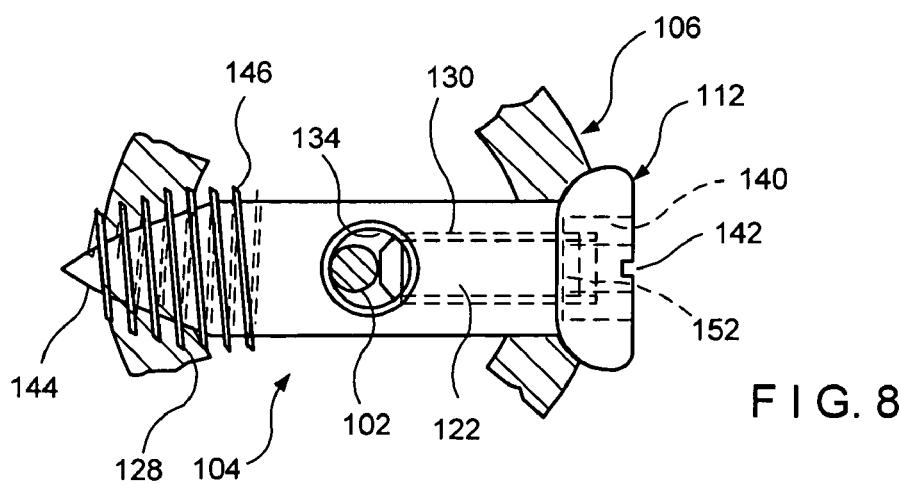
FIG. 8 is a top plan view of the nailing system taken along section plane 8-8 of FIG. 6.

In use, the particular number of screw assemblies 112 and their location along the length of the bone structure 106 can be determined by fluoroscopy or other techniques, and may be based on the type and size of the bone structure, the age of the injured person, the number of breaks, and so on. The screw assemblies 112 can then be installed at the determined locations by directly boring through the bone with the screw assemblies with an appropriate tool, such as a hex key connected to the chuck of a drill (not shown) or the like. In some circumstances, it may be desirable to drill pilot holes prior to transverse installation of the screw assemblies in the bone structure. Once in place, the screw assembly 112 is rotated until the alignment indicator slots 142 are aligned with the longitudinal direction of the bone structure 106 such that the receiving bore 134 is centered in the medullary canal 104 and also in alignment with the longitudinal direction of the bone structure, as shown in FIG. 8. Since the receiving bore 134 is within the bone structure 106, it may be difficult to view and align the receiving bore using fluoroscopy only. Accordingly, the alignment indicator slots 142 facilitate blind alignment of the first receiving 134 in the medullary canal.

Once the screw assembly 112 is in proper position, the hex rod 168 of the alignment jig is inserted into the hexagonal depression 140. The base member 162 is then rotated about the pivot joint 170 until the proximal surface 178 of the first leg 164 is in contact with the distal end 180 of the bone structure 106. In this manner, the exposed end of the hex rod 168 is in contact with the inner surface 175 of the second leg 166. In this position, the hex rod 168 is preferably substantially perpendicular to the second leg 166 and parallel to the first leg 164, as shown in FIGS. 11 and 12. The central bore 174 of the tubular guide member 172 is thus automatically aligned with the central axis 135 of the receiving bore 134 of the screw assembly 112. A drill bit 182 (shown in hidden line) is then inserted through the central bore 174 and the opening 176. Upon rotation by a rotary tool 184, such as a drill or the like, the drill bit 182 forms a hole 186 in the distal end 180 of the bone structure 106. It will be understood that the hole may additionally or alternatively be formed at the proximal end of the bone structure.

When the medullary canal has been reached, the drill bit is removed and an intramedullary rod 102 is inserted through the central bore 174, the opening 176, the hole 186, the medullary canal 104 (see FIGS. 6 and 12), and finally the receiving bore 134 of the screw assembly 112.

When multiple screw assemblies are to be placed at different positions along the length of the bone, a plurality of alignment jigs with different leg sizes and guide member positions can be used, as illustrated in FIGS. 13 and 14. The alignment jig 160A as shown is substantially similar in construction to the alignment jig 160 previously described, with the exception that the second arm 166A is shorter than the second arm 166, and the position of the tubular guide member 172 and opening 176 are at a different location on the first leg 164A to accommodate the extra width of the distal end 180 of the bone structure 106. The embodiment of FIGS. 13 and 14 is specifically adapted to accommodate bone growth of a patient.

In accordance with a further embodiment of the invention, the first leg 164 and/or the second leg 166 may be telescopic or otherwise adjustable in length for adapting to any bone size and screw assembly placement. In this manner, a single alignment jig can be used for a variety of different alignment requirements.

If multiple screw assemblies have been placed, the rod 102 is inserted through the receiving bore of each screw assembly as shown in FIG. 5. The particular position of the rod 102 with respect to the screw assemblies 112 can be verified through radiographic studies. The alignment jig 160 is then removed and the locking member 122 of each screw assembly is rotated until the rod 102 is clamped between the locking member 122 and the inner wall of the receiving bore 134 (see FIG. 8). In this manner, the intramedullary rod is securely fixed to the bone segments. In circumstances where bone growth may be impeded by multiple clamping positions of the screw assembly along the intramedullary rod, one or more of the screw assemblies may be left unclamped to provide for bone movement.

With the above-described arrangement, long bone structures with one or more breaks can be securely supported during the healing process. The system of the present invention is especially advantageous for small bone structures where it is impractical to insert a large diameter rod into a small bone or securely anchor a small diameter rod to the bone segments with an even smaller diameter screw since insufficient cross-pinning to isolate movement of the rod or to fix it in a desired position would result. By way of example, a screw assembly 112 in accordance with the present invention with a shaft diameter of 5 mm can be fixedly attached to a 2 mm diameter rod. Likewise, a screw assembly 112 with a shaft diameter of 6 mm can be fixedly attached to a 3 mm diameter rod, and so on. The particular sizes of screw assemblies and rod diameters can be adjusted to accommodate a wide variety of bone structures and conditions. The relatively large diameter of the screw assembly 112 enables it to span the medullary canal 104 and be securely fastened to opposite sides of a bone structure and to the intramedullary rod to thereby securely hold the bone segments together.

In addition, the present invention may be used in treatments involving both compression and non-compression modes. The compression mode would include fixing the intramedullary rod at multiple positions for maximum bone stability that in many cases may allow at least partial weight bearing on the affected limb. The non-compression mode would include fixing the intramedullary rod at a single position (or even no fixation at all) to the screw assembly while allowing longitudinal guided motion of the rod through the receiving bore of a second screw assembly. The receiving bore would thus serve as a guide to ensure only linear movement of the rod during bone growth or treatment procedures.

Figure 15:
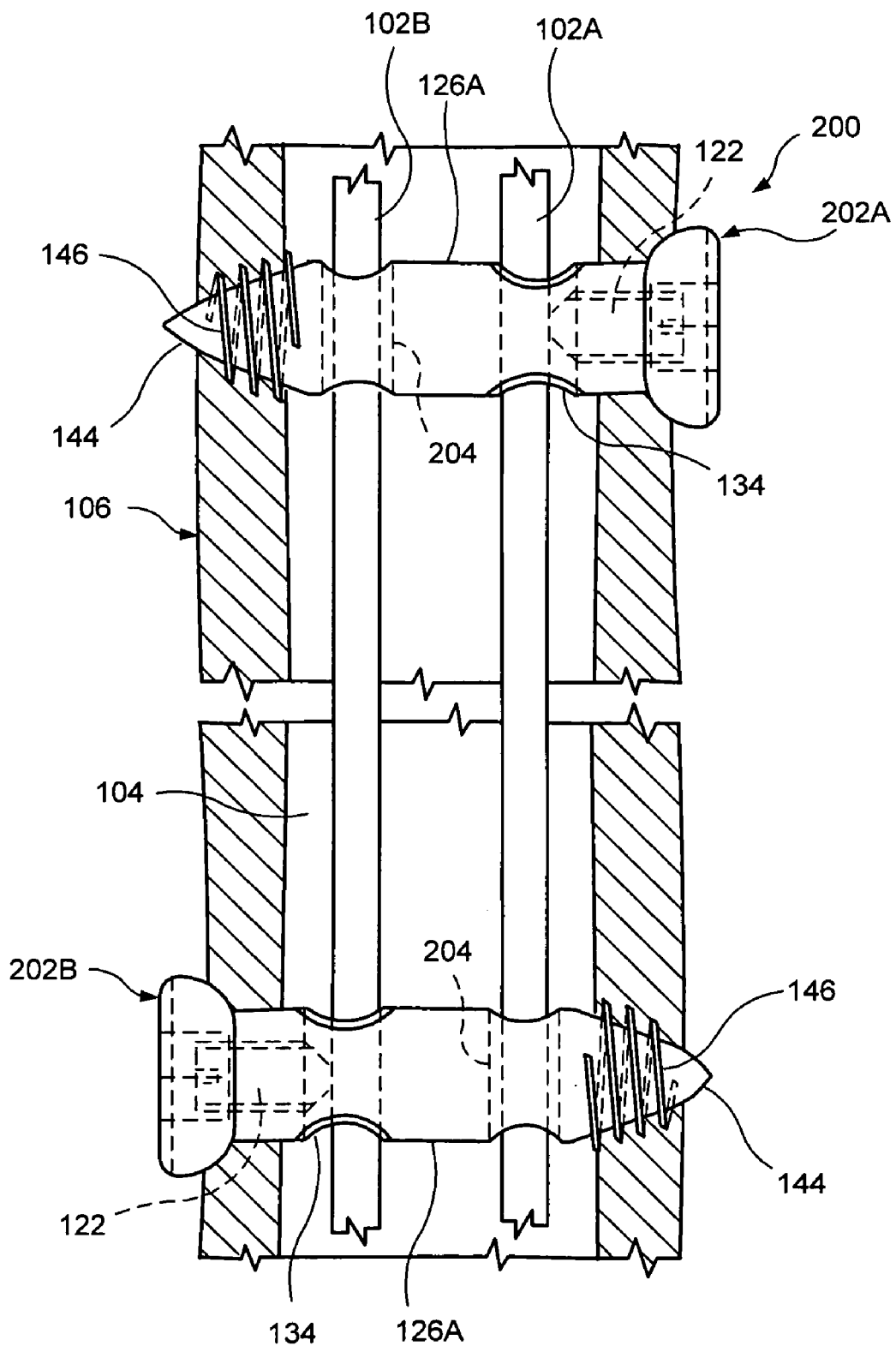
FIG. 15 is an enlarged front view of a nailing system in accordance with a further embodiment of the invention.

Turning now to FIG. 15, an intramedullary nailing system 200 in accordance with a further embodiment of the invention is illustrated. The system 200 is similar in construction to the system 100 previously described, with the exception that two intramedullary nails or rods 102A, 102B are secured within a medullary canal 104 of a bone structure 106 by a pair of screw assemblies 202A and 202B, respectively. As shown, the screw assemblies 202A and 202B extend through the bone structure 106 from opposite directions. Each screw assembly 202A, 202B is similar in construction to the screw assembly 112, with the exception that a second receiving bore 204 is provided in the shaft 126A between the receiving bore 134 and the conical section 144 to accommodate the extra intramedullary rod. The second receiving bore 204 is preferably parallel to the receiving bore 134. With this configuration, the rod 102A is secured to the screw assembly 202A in a manner previously described, and is adapted to slide freely through the screw assembly 202B via the second receiving bore 204. Likewise, the rod 102B is secured to the screw assembly 202B and is adapted to slide freely through the screw assembly 202A via the bore 204. As illustrated in FIG. 15, the rod or nail 102A is secured within the receiving bore of the screw assembly 202A. However, this rod can slide freely within a second receiving bore 204 of the second screw assembly 202B. In a similar manner, the nail or rod 102B is fixedly positioned within the first receiving bore 134 of the screw assembly 202B and can slide freely within the second receiving bore 204 of the screw assembly 202A. Such arrangement compensates for possible movement of one segment of the broken bone with respect to another bone segment, while assuring the required stability of the bone structure.

It will be understood that the term "preferably" as a used throughout the specification refers to one or more exemplary embodiments of the invention and therefore is not to be interpreted in any limiting sense.

In addition, terms of orientation and/or position as may be used throughout the specification, such as but not limited to: lateral, medial, longitudinal, inner, outer, front, rear, upwardly, downwardly, as well as their derivatives and equivalent terms, relate to relative rather than absolute orientations and/or positions.

It will be appreciated by those skilled in the art that changes could be made to the embodiments described above without departing from the broad inventive concept thereof. It will be understood, therefore, that this invention is not limited to the particular embodiments disclosed, but is intended to cover modifications within the spirit and scope of the present invention as defined by the appended claims.

What is claimed is:

1. A system for securing an intramedullary rod adapted for positioning at a medullary canal of a human bone in an orthopedic procedure, the system comprising:
    an intramedullary rod;
    a screw having a screw body extending between distal and proximal ends thereof, the screw body comprising a shaft with at least one receiving bore extending through the shaft transversely to its longitudinal axis and an internal cavity extending from the proximal end of the body along the longitudinal axis and intersecting said at least one receiving bore, said at least one receiving bore being adapted to receive the intramedullary rod,
    an alignment jig operably associated with the screw and the intramedullary rod, the alignment jig comprises a base member with a first leg and a second leg extending from the first leg, the second leg being adapted for engaging the internal cavity of the screw at the proximal end of the body, the first leg being adapted to contact a bone structure and having an opening coincident with the at least one receiving bore of the screw to thereby align the intramedullary rod with the at least one receiving bore within a medullary canal of the bone structure;
    whereby in an assembled condition said at least one receiving transverse bore is adapted for positioning within the medullary canal so as to receive the intramedullary rod which passes through said canal in such a manner that longitudinal axes of the intramedullary rod, said at least one receiving bore and the opening of the first leg coincide.

2. A system according to claim 1, wherein the alignment jig further comprises a tubular guide member extending from the first leg and coincident with the opening, the tubular guide member being adapted to receive a drill bit adapted for forming a hole in the bone structure in alignment with the at least one receiving bore and to receive the intramedullary rod for guiding the rod toward the at least one receiving bore.

3. A system according to claim 2, wherein the alignment jig further comprises a bar connected to the second leg, the bar being adapted to fit within the internal cavity of the screw.

4. A system according to claim 3, wherein the bar is pivotally connected to the second leg.

5. A system according to claim 4, wherein the first and second legs are substantially perpendicular to each other.

* * * * *